United States Patent
Lueck

(12) 
(10) Patent No.: US 6,306,291 B1
(45) Date of Patent: Oct. 23, 2001

(54) AUTOMATIC SILT DENSITY INDEX APPARATUS

(76) Inventor: Stanley R. Lueck, 715 El Paso, Farmington, NM (US) 87401

( * ) Notice: Subject to any disclaimer, the term of this patent is extended or adjusted under 35 U.S.C. 154(b) by 0 days.

(21) Appl. No.: 09/447,678

(22) Filed: Nov. 23, 1999

Related U.S. Application Data

(60) Provisional application No. 60/110,047, filed on Nov. 24, 1998, and provisional application No. 60/154,156, filed on Sep. 15, 1999.

(51) Int. Cl.$^7$ .................................................. G01N 15/02
(52) U.S. Cl. ........................... 210/90; 210/97; 210/103; 210/132; 210/137; 210/203; 210/206; 210/341; 73/61.63; 73/61.73; 73/863.23
(58) Field of Search .................................. 210/85, 87, 90, 210/97, 103, 120, 132, 137, 203, 206, 341, 149; 73/61.73, 61.63, 61.64, 863.23

(56) References Cited

U.S. PATENT DOCUMENTS

| | | |
|---|---|---|
| Re. 29,454 * | 10/1977 | Ashmead et al. . |
| 3,499,315 * | 3/1970 | Marino . |
| 3,979,292 * | 9/1976 | Kuhn . |
| 4,151,086 * | 4/1979 | Brooks . |
| 4,282,093 * | 8/1981 | Haga et al. . |
| 4,341,124 | 7/1982 | Rodgers et al. . |
| 4,554,822 | 11/1985 | Eisenhauer et al. . |
| 4,583,396 | 4/1986 | Hunt et al. . |
| 4,765,963 | 8/1988 | Mukogawa et al. . |
| 4,786,473 | 11/1988 | Mukogawa et al. . |
| 5,198,116 | 3/1993 | Comstock et al. . |
| 5,253,514 | 10/1993 | Kaakinen . |
| 5,445,735 | 8/1995 | Kaakinen . |
| 5,807,427 * | 9/1998 | Welch . |
| 6,077,435 * | 6/2000 | Beck et al. . |

OTHER PUBLICATIONS

AquaLynx™ 400 Enahanced SDI Monitor™, Mar., 1999, RODI Systems.
AquaLynx™ 400 Enhanced SDI Monitor™, Sep., 1999, RODI Systems.
"Predict RO Membrane Fouling Before It's Too Late!", RODI News, Apr. 1999, RODI Systems.

* cited by examiner

Primary Examiner—Joseph W. Drodge
Assistant Examiner—Terry K. Cecil
(74) Attorney, Agent, or Firm—Joseph Barrera; Rod D. Baker

(57) ABSTRACT

An apparatus for monitoring particulates in a liquid stream and the rate at which the particulates foul a filtering medium, generally a reverse osmosis membrane, to determine at what point in time the filtering medium should be cleaned or replaced. The apparatus includes a monitoring filter unit having a plurality of filter portions. The pressure drop across each filter portion, through which a sample of the feed stream is passed, is monitored. Fouling of a filter portion by accumulated particulate thereon causes an increase in the pressure drop across the filter unit. The increasing pressure drop is monitored as an indicator of the correlative or correspondent fouling of the main filtering medium to be protected. Different filter portions in the filter unit are successively used as each becomes fouled, allowing continuous monitoring for extended periods of time between filter media changes in monitoring filter unit.

13 Claims, 8 Drawing Sheets

AUTOMATIC SILT DENSITY INDEX APPARATUS

CROSS-REFERENCE TO RELATED APPLICATIONS

This application claims the benefit of the filing of U.S. Provisional Patent Application Ser. No. 60/110,047, entitled "Automatic Silt Density Index Apparatus," filed on Nov. 24, 1998, and U.S. Provisional Patent Application Ser. No. 60/154,156, entitled "Automatic Silt Density Index Apparatus," filed on Sep. 15, 1999, and the specifications thereof are incorporated herein by reference.

BACKGROUND OF THE INVENTION

1. Field of the Invention (Technical Field)

The present invention relates apparatus and methods for measuring the amount of particulate matter in liquid feed streams, and more particularly to apparatus for measuring the rate at which particulate matter in an aqueous feed stream will clog or foul filters, specifically reverse osmosis membranes.

2. Background Art

Due to the increasing shortfall in fresh water supplies, the use of reverse osmosis (RO) systems to desalinate salt and brackish water has been on the rise. In concept, RO is a simple process. Water is forced through a membrane under pressure. The membrane rejects both dissolved and suspended solids producing a very pure permeate. The process may be described as filtration on a molecular or ionic level. Unlike most filtration processes, however, RO is not simple to monitor. Of particular importance is the need to monitor the feedwater going to the RO unit to determine its potential of clogging or fouling the membrane surface.

Monitoring the fouling tendency of an RO membrane is a challenge. Fouling tendencies of the feedwater are usually not noticed until the RO membranes are in need of cleaning. This results in expensive downtime or, worse yet, membrane replacement. Numerous methods have been used to measure the fouling tendency of feedwaters. These include turbidity, particle counting, and silt density index (SDI). It is difficult to correlate turbidity and particle counting to membrane fouling since they do not directly measure the fouling or "plugging" nature of the particles in suspension. SDI has proven useful in indicating fouling tendencies, however, the manual SDI method is tedious and time-consuming.

The American Society for Testing and Materials (ASTM) has published procedures for a simple test to determine the silt density index (SDI) of RO feedwaters. The ASTM test involves placing a 47 mm filter disk (with 0.45 micron pore size) in a filter holder. The feedwater is passed through the filter at 30 psi. The amount of time required (t1) for the first 500 ml of feedwater to pass through the filter is recorded. The feedwater is allowed to continue to pass through the filter at 30 psi for 15 minutes. At the end of the 15 minute period, the time required (t2) for another 500 ml of water to pass through the filter is recorded. The SDI is calculated using the following equation:

$$SDI = (100 \times (1 - (t1/t2)))/T$$

Where:

t1 = elapsed time for first 500 ml
t2 = elapsed time for last 500 ml
T = 15 minutes The SDI value will range from 0 to 6.7. Any value less than 4 is considered suitable for RO feed from a membrane fouling standpoint.

Although it may seem archaic, the SDI test is still recognized as one of the best ways to predict the fouling potential of a feedwater on RO and nanofiltration membranes. Drawbacks to the conventional way of measuring SDI is the fact that it is a manual test requiring an operator's undivided attention, and the method is time consuming, requiring 30 minutes or more per analysis. Most RO facilities are fortunate if the SDI of the RO feedwater is checked once per day.

Automated SDI monitors developed to date also have drawbacks. Eisenhauer et al., U.S. Pat. No. 4,554,822 requires complicated equipment for the handling of filters in the form of rolls for the replacement of the filter after each measurement. Also, this automated SDI monitor still requires 20 minutes for data collection, and provides no information on the nature of the particulates within the feedwater that will eventually plug or foul RO membranes. Kaakinen, U.S. Pat. No. 5,253,514, appears to solves these problems by measuring at constant pressure the change in flow rate ($Q_t$) of the feedwater through the filter at specific time intervals. This system allows a SDI measurement to be obtained in about 5 minutes. In contrast, the present invention has the capability of obtaining a SDI measurement every few seconds, and thus allows for virtually continuous monitoring of particulates in the feed stream. The present invention stores this data and/or uses the data to calculate a real-time fouling rate at the RO membrane.

One disadvantage of the Kaakinen device is that it does not provide for the change in zeta potential as particulates build up on the test filter. Many cases have been documented in which the conventional SDI test was not effective in identifying the fouling potential of RO feedwater. This is due, in large part, to the fact that the conventional SDI test does not simulate the chemical changes that occur in RO systems. As feed water permeates through the membrane, the dissolved solids concentration increases in the boundary layer next to the membrane. Depending upon feedwater quality, changes in hardness, salinity, and pH may also occur. These changes modify the electrostatic charges (zeta potential) which keep small particles suspended thus allowing them to coagulate and foul the membrane and membrane feed spacer. The present invention has the capability of solving this problem by adding at least one chemical reagent up stream of the test filter so that the zeta potential at the test filter more accurately correlates with the zeta potential at the surface of the RO membrane. The similarity in the zeta potential at the test filter and the RO membrane allows the system to more accurately monitor the fouling conditions at the RO membrane.

SUMMARY OF THE INVENTION (DISCLOSURE OF THE INVENTION)

A primary object of the present invention is to monitor the amount of suspended particulate in a feed stream, particularly RO feedwaters.

Another object of the invention is to determine the time it will take for the suspended particulates to clog or foul an RO membrane.

Another object of the invention is to determine an appropriate time schedule to clean or replace an RO membrane.

A primary advantage of the present invention is the evaluation of the fouling conditions at the RO membrane by comparison of the fouling conditions at a test filter.

Another advantage of the present invention is that continuous monitoring of the rate of increase in pressure drop across the test filter provides real-time RO membrane fouling tendency data.

Another advantage of the present invention is that multiple filter media portions provide the means to measure the fouling conditions or the amount of particulate in the feed stream at different times without the operator having to change the filter medium after every SDI measurement.

Another advantage of the present invention is that it is easy to install, easy to operate, and sells for a fraction of the cost of other automatic SDI testing equipment.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

The present invention is an automatic silt density index (SDI) monitor that monitors various process signals, calculates parameters based upon these signals, displays data on an LCD display, and stores data in its internal memory. The invention comprises a flow sensor and control, pressure sensor and control, and series of solenoid valves in signal (e.g. electrical) communication with a microprocessor-based controller. In the preferred embodiment, a unique filter holder allows the apparatus to perform multiple SDI tests by providing a plurality of filter portions before replacement of the filter media becomes necessary. Moreover, the replacement of the filtering media takes approximately only two minutes, and the filtering media costs less than that used for the manual SDI test. The apparatus is easy to install, easy to operate, and may be manufactured for a fraction of the cost of other automatic SDI testing equipment.

Figure 1:
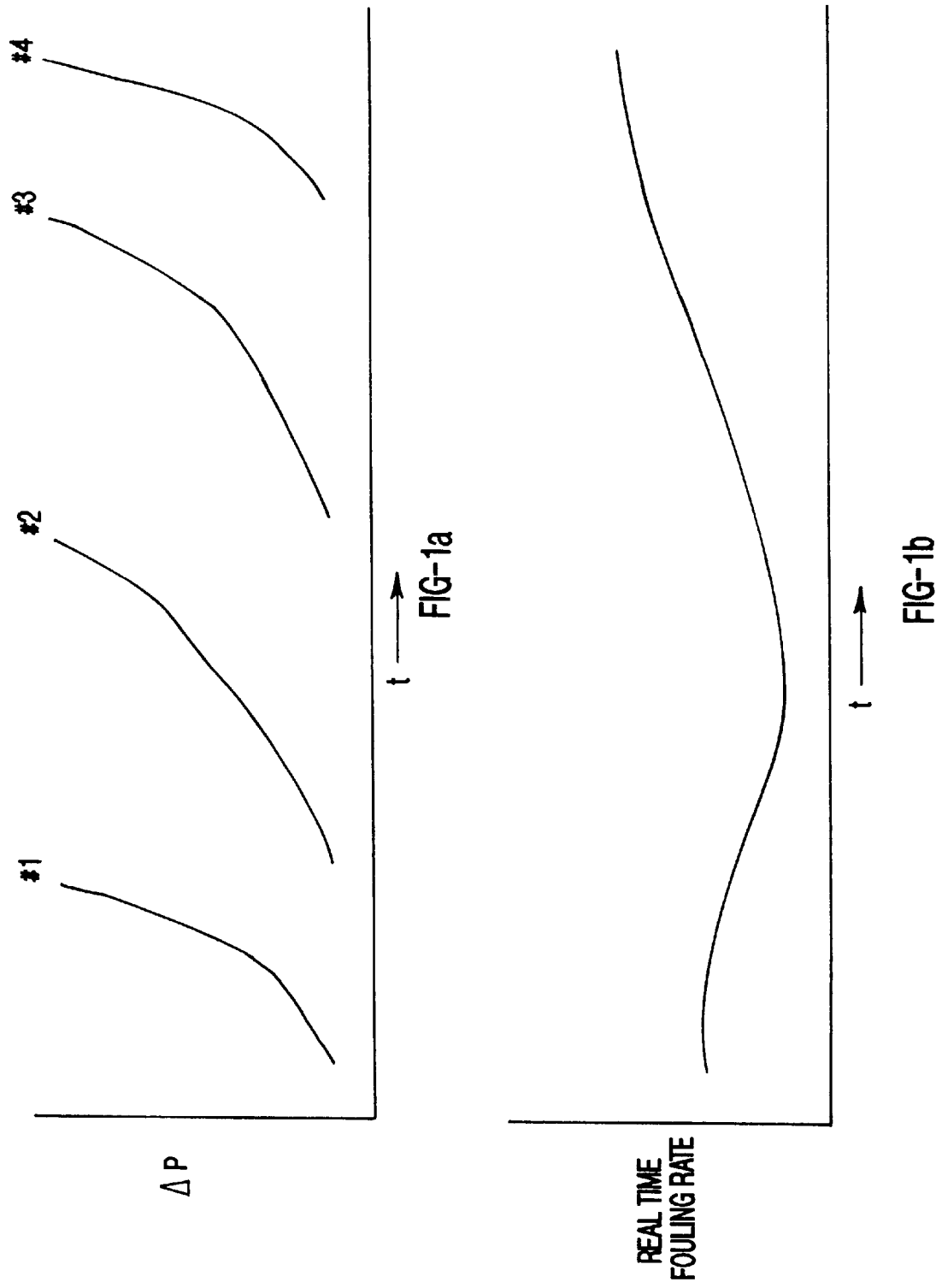
FIG. 1A is graphs of filter flux decline and real-time fouling rate created by the computer program in the enhanced automatic SDL monitoring apparatus according to the present invention.
FIG. 1B is a graph of discrete test data from FIG. 1 normalized into a continuous output of membrane fouling rate.

The invention can be programmed to perform SDI monitoring at prescribed intervals, at prescribed times of day, or continuously. The invention can be programmed to switch automatically from one filter portion to another filter portion so as to provide continuous data until the filter unit requires a replacement filter. The apparatus of the invention controls flow and measures pressure drop across the filter unit to determine the fouling rate of the filter media. In contrast, all prior SDI systems control pressure while monitoring flow rate. SDI value data is stored with time and date, and relay and analog outputs are available to interface with other control and recording equipment. In addition to calculating standard SDI values, the invention measures and calculates differential pressure rates ($\Delta P/\Delta T$), that is, the how the pressure drop across a respective filter portion changes with time. The microprocessor-based controller 30 also mathematically correlates the differential pressure rate data to provide information on the real time fouling tendency of the RO feedwater stream. The differential pressure rate data, as well as other system data, can be downloaded to any PC and viewed in graphical form. Comparison of these differential pressure rate curves, FIG. 1 provides information on the fouling propensity on the RO membrane of the feed stream. This type of information cannot be obtained from SDI values alone.

FIG. 1A graphically illustrates change in pressure drop, as a function of time, for four successively tested filter portions in a single filter unit. The increasing slope of each curve shows how the change in pressure drop across a given filter portion increases with time. The increase in pressure drop results from the increase in fouling that occurs at the surface of the filter portion as the feed stream flows through the filter portion. For example, in a typical continuous run, the feed stream initially passes through filter portion No. 1. As filter portion No. 1 fouls, the rate of pressure drop increases (as shown by the increase in slope) to a selected maximum value. At such a time a valve to filter portion No. 1 closes and a valve to filter portion No. 2 is opened. The feed stream then flows through filter portion No. 2 until the maximum pressure value is reached, at which time a valve closes to interrupt feed stream flow to filter portion No.2, and a valve opens to allow flow to filter portion No. 3. The process is repeated for filter portions No. 3 and No. 4. When filter portion number 4 is fouled, as determined by the pressure drop across it obtaining the maximum value, the operator opens the entire filter unit and replaces the filter media in the filter portions. This process control option allows the SDI monitor according to the invention to record SDI data over a relatively long time period, as well as record data on a continual basis.

FIG. 1B represents a mathematical correlation of the data collected in FIG. 1A, and depicts the real-time fouling rate at the RO membrane. Integration of this curve provides actual fouling information at the RO membrane.

Figure 2:
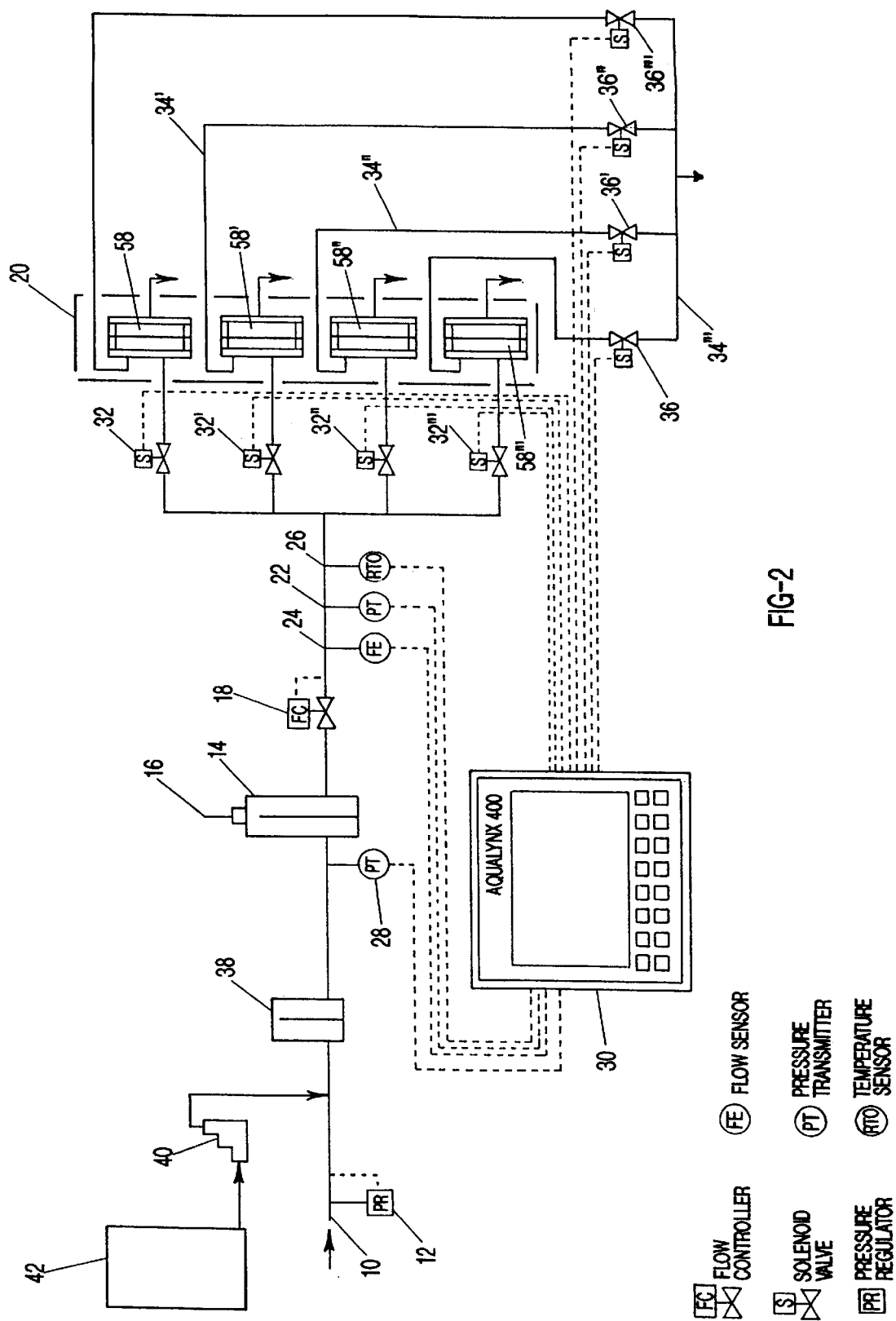
FIG. 2 is a schematic diagram of an embodiment of the SDI monitoring apparatus of the present invention.

Attention is invited to FIG. 2, which schematically illustrates a preferred embodiment of the apparatus of the invention. The apparatus is devised to tap a sample of the feed stream from the main feed stream flow, and divert the sample to the monitoring apparatus of the invention. The feed stream may be any flowing liquid, although the invention is particularly suited to the monitoring of aqueous feed streams to be treated by reverse osmosis. The main flow of the feed stream continues on to the main RO membrane assemblies (not shown), while a sample of the feed stream is pumped through a feed stream conduit 10 for conveyance to the apparatus of the invention. The pressure of the feed stream conveyed in the feed stream conduit 10 is maintained at a selected minimum pressure by a pressure regulator 12. A pressure sensor 28 is in operative conjunction with regulator 12 to maintain the desired minimum pressure of the conveyed feed stream. The feed stream passes through a gas separation chamber 14 whereby air and other entrained gases are separated from the feed stream and removed from the system through vent orifice 16. The feed stream then moves through a flow controller 18 that maintains a constant discharge of fluid to a filter unit 20 having at least one, preferably a plurality (for example, four) filter portions 58, 58', 58'', 58'''. A flow sensor 24 monitors the discharge of the feed stream to permit regulation by the flow controller 18. The feed stream conduit includes a manifold whereby the feed stream may be directed to any one, or any combination, of filter portions 58, 58', 58'', 58'''. The filter portions 58, 58', 58'', 58''' are hydraulically disposed in parallel, so that by means of solenoid valves 32, 32', 32'', 32''', the fluid stream may be selectively directed to the discrete filter portions. Each of the filter portions 58, 58', 58'', 58''' contains filter media, such as filter paper or ceramic filter disks. Pore size openings of the filter media can be varied depending upon the application and the nature of particulates in the feed stream. An optional temperature sensor 26 measures the temperature of the feed stream.

The apparatus regulates the constant flow of the feed steam through the filter unit 20 while measuring the pressure drop across the filter unit, or, more specifically, the pressure drop across each of the filter portions 58, 58', 58'', 58'''. The detected pressure drop across each one of the filter portions 58, 58', 58'', 58''', as each filter portion in its successive turn becomes fouled, permits the feed stream to be redirected to the next unfouled filter portion. The pressure of the feed stream on the back side 44 of the filter unit 20 is measured by one or more pressure sensors 22. The pressure on the front side 50 of the filter unit 20 is maintained at atmospheric pressure. Thus, the pressure sensor 22 signals the microprocessor-based controller 30 when a selected maximum pressure across the unit 20 is sensed, and the microprocessor-based controller 30 initiates the closure of a first one 32 of the solenoid valves 32 and initiates the opening of a second one 32' of the solenoid valves, to permit the continued uninterrupted feed stream flow through the monitoring unit 20. The process may be repeated until all the filter portions 58, 58', 58'', 58''' are fouled. When the maximum selected pressure across the filter unit 20 is sensed by the sensor 22, after feed stream flow has been directed through the ultimate filter portion 58''', the microprocessor-based controller 30 may actuate an alarm to indicate the need to open and change the filter media in the filter unit 20. In sum, the filter unit 20 includes a plurality of filter portions 58, 58', 58'', 58''' disposed hydraulically in parallel, and the valves 32, 32', 32'', 32''' permit the operator to selectively direct the sample feed stream to selected ones of the filter portions, whereby the sample feed stream is serially directed to successive filter portions to prolong the need to open the filter unit and replace filter media.

The measured difference between the back pressure and front pressure of the filter unit 20 is transmitted to and stored in the digital microprocessor-based controller 30. As the filter medium in a particular filter portion 58 fouls, the pressure on the back side of that filter portion increases, resulting in an increase in the pressure drop across the filter unit. The rate of change of the pressure drop, as calculated by the microprocessor-based controller 30, is an indicator of the tendency of the feed stream to foul the RO membrane of the monitored main treatment process, and thus provides the necessary information to determine RO membrane maintenance schedules. The correlation between the monitored fouling of successive ones of the filter portions 58, 58', 58'', 58''' and the corresponding fouling of the RO Membranes to be cleaned and protected, is a central advantage object of the invention. The further ability to conduct SDI data and measure changes in pressure differential across the test filter unit 20 in a continuous mode, to provide constant real-time fouling tendency data, is an advantage of the invention over known monitoring devices.

The microprocessor-based controller 30 performs several functions. The microprocessor-based controller 30 is a central processing unit. The best controller for use with the invention is the Aqualynx 400 Enhanced SDI Monitor manufactured by and available from RODI Systems, Inc., of Aztec, N.M., USA. The operator of the invention can program the microprocessor-based controller 30 to sample the main feed stream and convey the sample to the apparatus at specific times and for specific durations. For example, when sampling a feed stream with lower fouling tendencies, tests may be separated by relatively longer intervals (e.g., one to three tests per day). Tests may also be initiated manually or automatically based upon other events, such as after a filter back-wash. SDI results and pressure differentials are stored in the microprocessor-based controller 30 along with time and date. The data may be downloaded via a serial port to a personal computer to be stored, or fouling rate data may be calculated and displayed in graphical form. Also, the microprocessor-based controller 30 may feature alarms to alert the operator if certain operational conditions (e.g. excessive feed line pressure, excessive pressure drop across a filter portion, excessive temperature, precipitous pressure drops, and the like) are present. Relay and analog outputs allow the apparatus to interface with other control and recording equipment. The microprocessor-based controller 30 stores operational data such as inlet pressures, flow rates and temperatures for each sample feed stream by means of the sensors 22 and 28, 24, and 26, respectively.

The microprocessor-based controller 30 also allows the operator to select which portion of the filter media is used for a particular SDI test through pre-programmed control of selected solenoid valves 32, 32', 32'', 32'''. In practicing the invention, a typical example of the direction of the feed stream is accomplished by opening and closing successive ones of the selected solenoid valves 32, 32', 32'', 32''' to serially direct the stream first to one filter portion 58, and then when the pressure drop across filter portion 58 indicates that it is fouled, to direct the stream only to the next filter portion 58', and so on.

Figure 3:
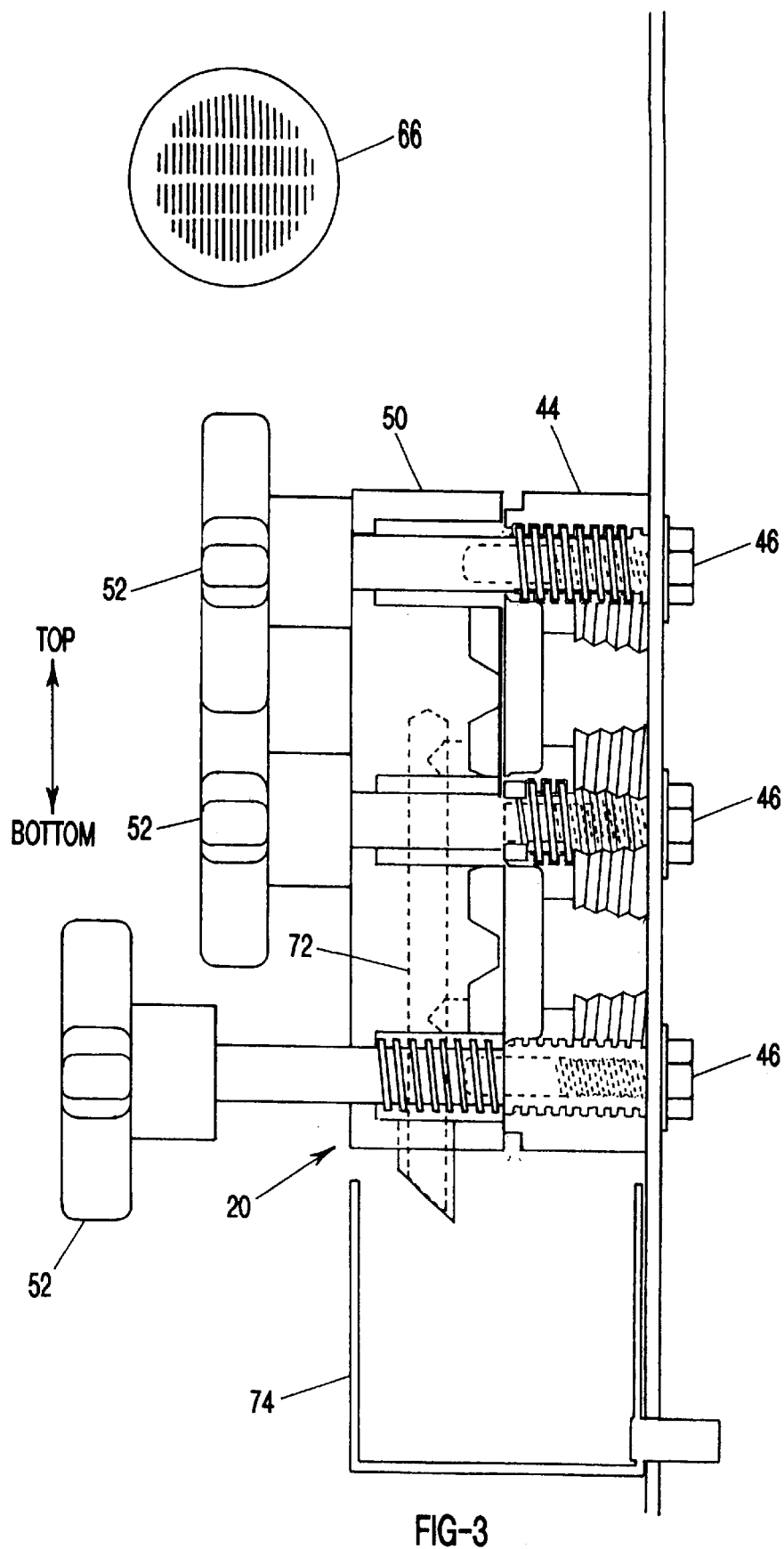
FIG. 3 is an enlarged sectional side view of the filter unit of the embodiment of FIG. 2.
Figure 4:
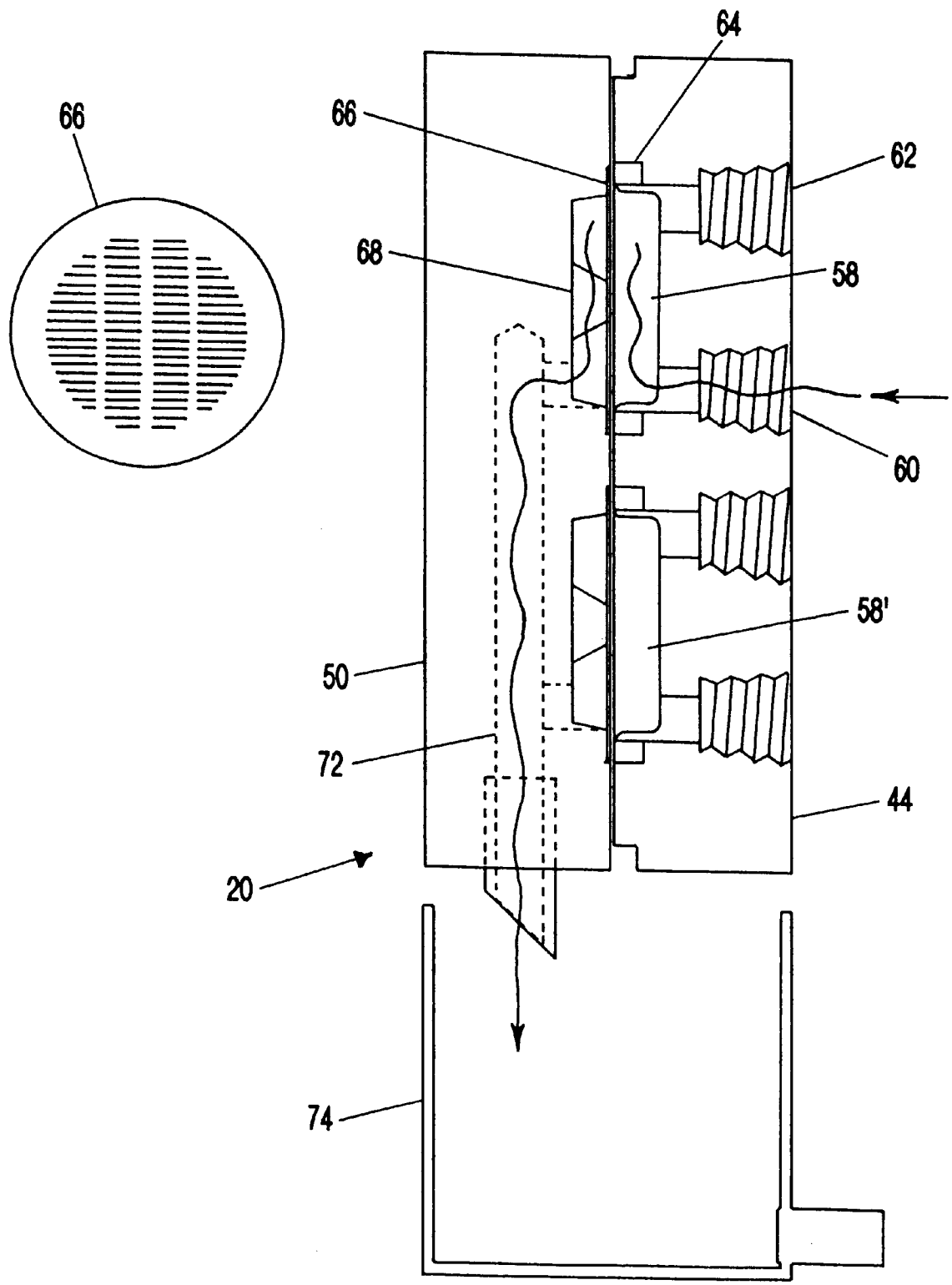
FIG. 4 is an enlarged sectional side view of the filter unit of FIG. 3, illustrating the flow of the feed stream through the unit.
Figure 5A:
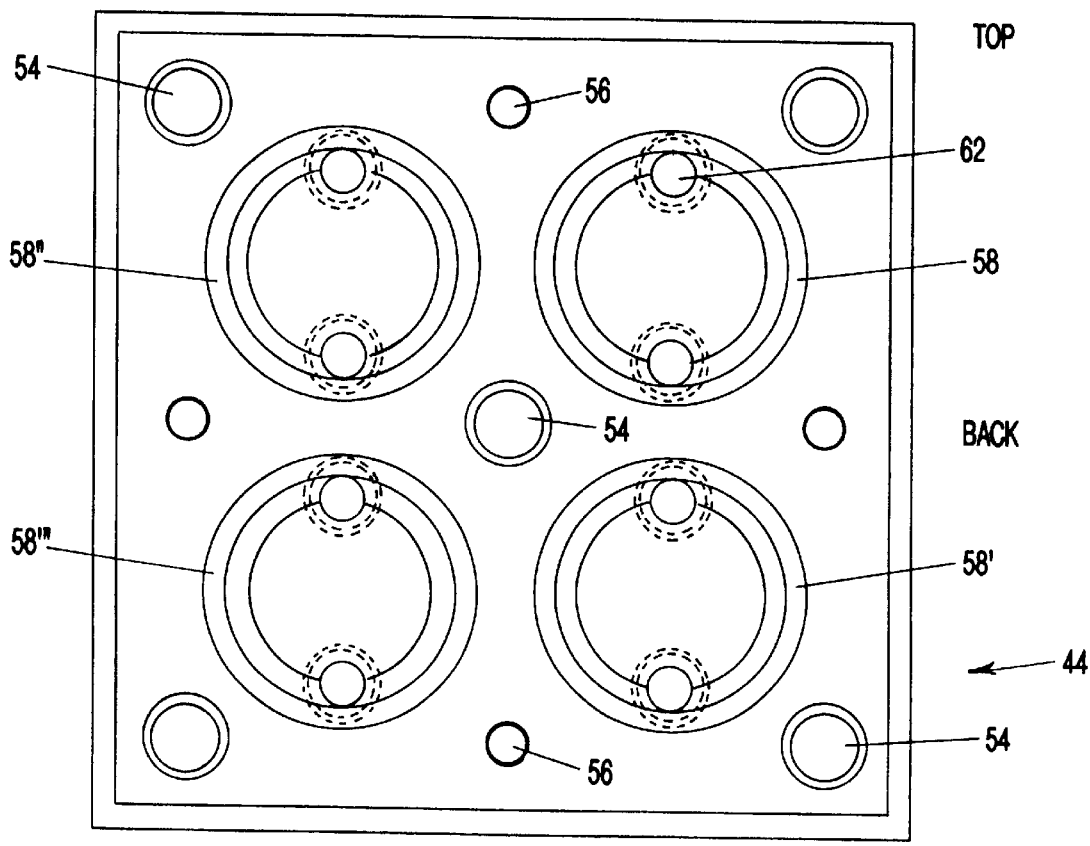
FIG. 5A is a back view of the filter unit of FIG. 3.
Figure 5B:
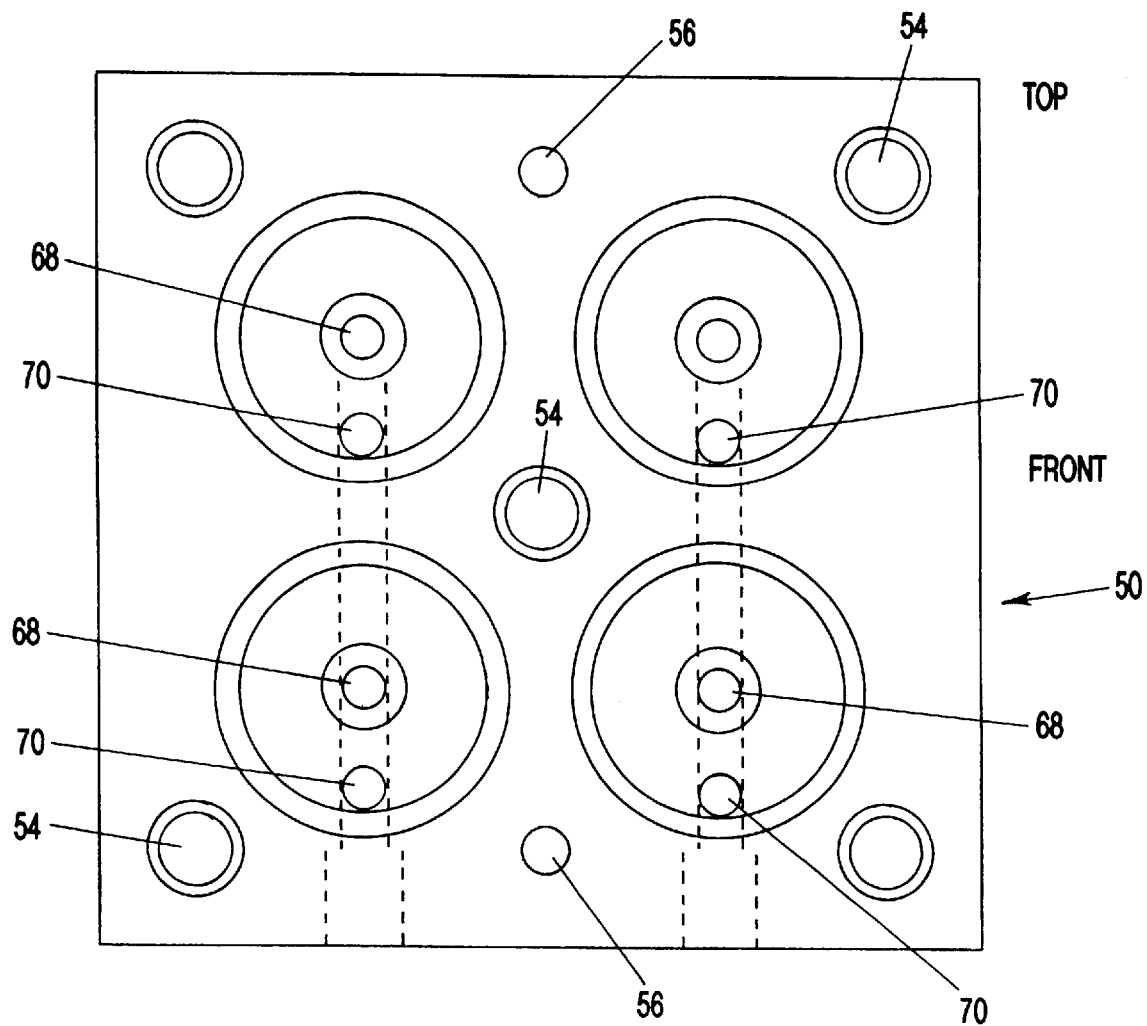
FIG. 5B is a front view of the filter unit of FIG. 3.

FIG. 3 provides an enlarged cross sectional view of a single filter unit 20, including therein the preferred plurality, preferably four, of filter portions 58, 58', 58'', 58'''. The filter unit 20 includes a back 44 and a front cover 50. The back 44 of the unit 20 is mountable to any instrument housing by means of the mounting bolts 46 threaded into the unit 20 at four locations 48, as seen in FIG. 5A. The front cover 50 of the filter unit 20 is mounted to the back 44 by means of the hand-tightened mounting bolts 52 which are threaded into the back 44 of the filter unit 20 at five locations 54, also as seen in FIG. 5A. Registration pins 56 on the front 50 of the filter unit ensure that the front 50 of the unit 20 is properly aligned when the unit is assembled for use. Reference is made to FIG. 4. The back 44 of the filter unit is equipped with the plurality of filter portions 58, 58', 58", 58"' including the filter media such as paper. Each one of the filter portions 58, 58', 58", 58"' has an inlet 60 and a vent 62. Each one of the filter portions 58, 58', 58", 58"' is sealed against liquid leakage by means of an O-ring 64. The front 50 of the filter unit 20 has filter supports 66 that correspond in location to the locations of the filter portions 58, 58', 58", 58"' on the back 44 of the filter unit. The filter medium for each filter portion is disposed between the associated filter support 66 and the front 50 of the filter unit 20. The filter supports 66 themselves are supported by a center post 68. The area behind each filter support 66 is equipped with an outlet 70 in fluid connection with a corresponding outlet channel 72 as seen in FIGS. 4 and 5. This allows the filtered feed stream sample to enter the drain pan 74.

When the filter medium, such as a paper filters with select pore size, in all the filter portions 58, 58', 58", 58"' requires replacement, the filter unit 20 is opened to facilitate the replacement. The operator unscrews the hand bolts 52 to separate the front cover 50 from the back side 44 of the filter unit 20. The fouled filter media is removed, new filter media is placed against the filter supports 66, and the filter unit 20 is reassembled by replacing the cover 50.

In one embodiment of the invention, the back of each of the filter portions 58, 58', 58", 58"' can be vented through a corresponding port 62 as the feed stream enters the filter portion through port 60, as seen in FIG. 4. Referring to FIG. 2, the corresponding vents 34, 34', 34", 34"' are controlled by selected actuation of the solenoid valves 36, 36', 36", 36"'. The downstream solenoid valves 36, 36', 36", 36"' close after all the air has been removed from the back portion of the filter 20 (that is, air enters the back of each of filter portions 58, 58', 58", 58"' following replacement of the filter media). The fouled filter media can be returned to a licensed laboratory for particulate analysis. This valuable feature provides data on the chemical nature and amount of the various types of particulates present in the sampled feed stream. Based upon this information, reverse osmosis experts can make valuable recommendations on the types of cleaning chemicals and procedures that should be utilized in the main treatment system.

A further embodiment of the invention improves the correlation between the test filter fouling and the correspondent fouling of the protected RO membranes of the main system. This embodiment includes components for modifying the zeta potential of the sample feed stream flowing into the filter unit 20, which include a source of chemical reagent in fluid communication with the feed conduit 10, and a pump for adding a chemical reagent from the source into the feed conduit. As feed water permeates through an RO membrane, the dissolved solids concentration increases in the boundary layer adjacent to the membrane. Depending upon feed stream quality, changes in hardness, salinity, and pH may also occur. These changes modify the electrostatic charge (zeta potential) which maintain small particles in suspension' reduction in zeta potential allows the particles to coagulate and foul the membrane and membrane feed spacer. The present invention permits the operator to adjust the zeta potential at the filter unit 20 to more closely simulate the zeta potential conditions at the RO membrane in the main system. This adjustment may be accomplished by changing the salinity, pH level, or hardness of the sample feed stream, depending upon the chemical composition of the raw feed stream. Adjusting the zeta potential in the filter unit 20 to be similar to that at the RO membrane permits more accurate monitoring of the fouling conditions at the RO membrane.

Figure 6:
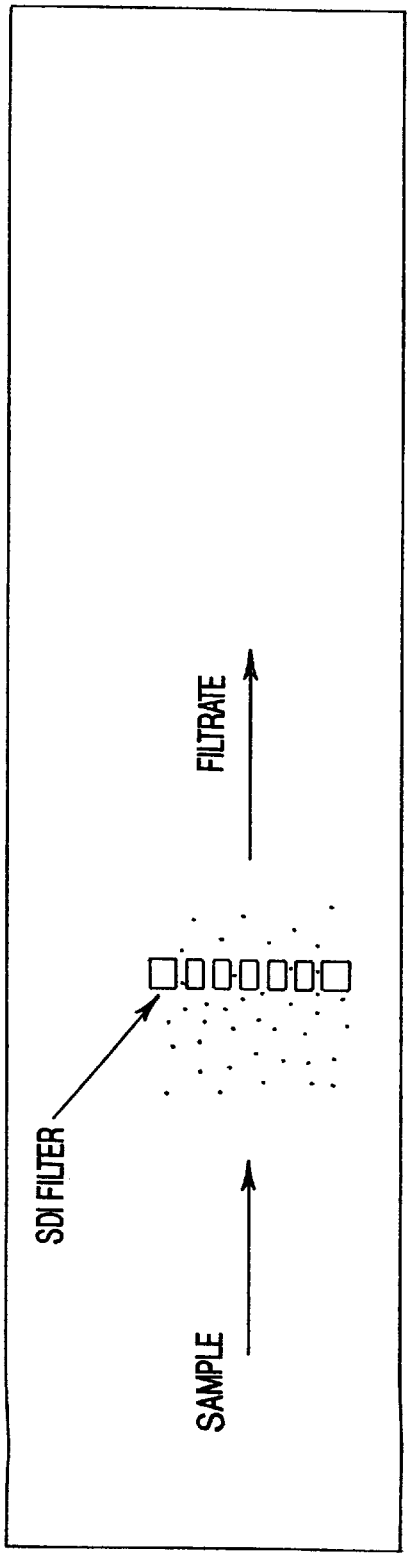
FIG. 6 is a diagram illustrating a conventional SDI test where the zeta potential of the feed stream is not chemically modified, thus small particles stay in suspension and pass through the SDI filter.
Figure 7:
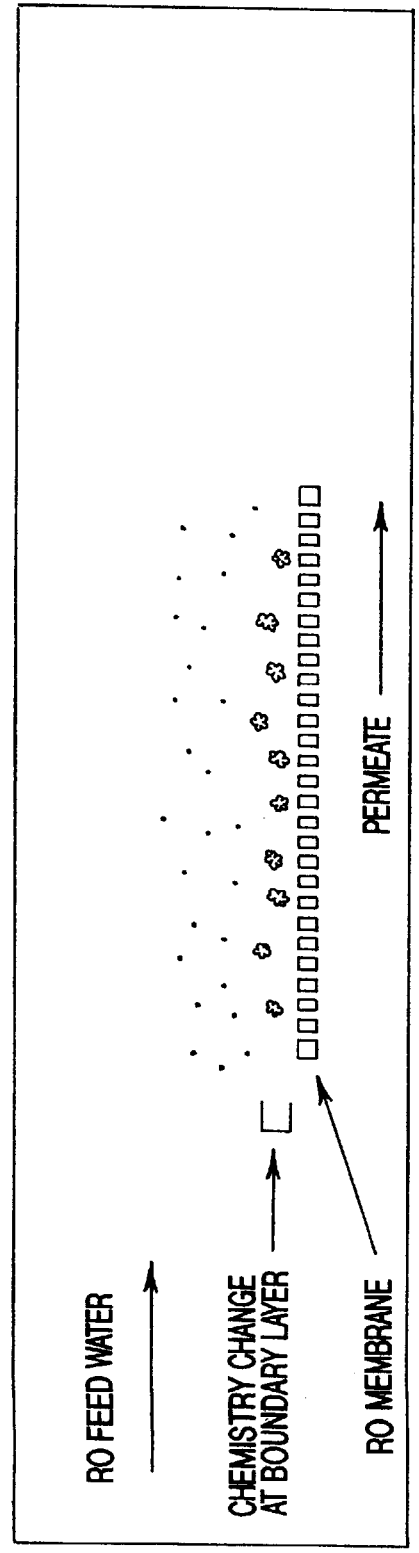
FIG. 7 is a diagram illustrating how suspended solids inherently coagulate at the surface of the RO membrane as the zeta potential is modified.
Figure 8:
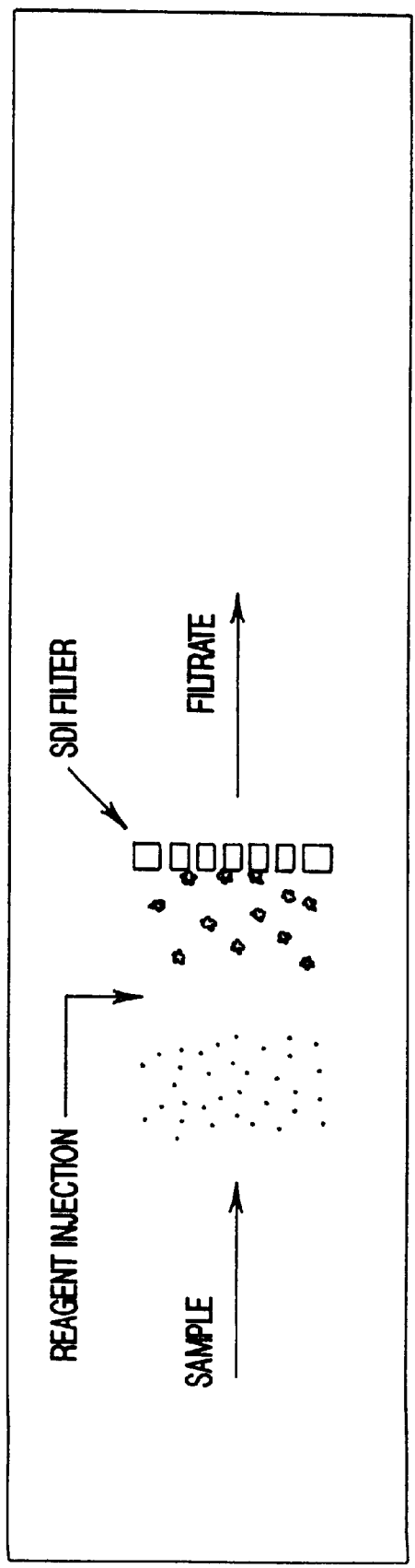
FIG. 8 is a diagram illustrating how, in an enhanced SDI test according to the present invention, with zeta modification chemistry the small particles coagulate.

Known SDI monitors do not adjust the zeta potential of the feed stream. Consequently, small particles that would foul an RO membrane pass through the test filter and thus are not detected or accounted for by the SDI monitor, illustrated by FIG. 6. As the small particles collect on the surface of the RO membrane the change in zeta potential at the surface causes the particles to coagulate, as seen in FIG. 7. In the present invention, and as indicated in FIG. 8, the addition of chemical reagents to the feed stream simulates the conditions on the RO membrane. Therefore, most if not all of the particulate matter that exists in the main feed stream is detected and accounted for by the apparatus of the invention.

This zeta potential modification embodiment of the invention is similar in every respect to the preferred embodiment previously described, except this second embodiment apparatus simulates the change in zeta potential with time as the RO membrane fouls. No other SDI system has the capability of simulating the change in zeta potential at the RO membrane as the RO membrane fouls. According to the invention, at least one chemical reagent is injected into the feed stream sample upstream for the monitoring components. Referring again to FIG. 2, it is seen that a supply of reagent 42 is disposed upstream from the filter unit 20, so that the zeta potential at the filter unit more accurately correlates with the zeta potential at the surface of the RO membrane in the main treatment system.

An injection pump 40 adds small quantities of a chemical reagent or reagents 42, such as chloride, into the feed stream in the feed stream conduit 10 before the stream flows to the filter unit 20. Suitable reagents useable in the practice of the invention include sodium chloride, calcium chloride, magnesium chloride, and sodium hydroxide, for changing the salinity, hardness, or pH of the sample feed stream. Also, it may optionally be desirable to add small amounts of known coagulant chemical reagents, used to induce coagulation of suspended particulates in aqueous feedwaters, (such as polyaluminum chloride) to induce coagulation in the stream. Coagulated particulates are then captured in the filter unit to allow the quantification and evaluation of particulates in the feed stream.

The feed stream preferably passes through a mixer 38 following injection of the chemical reagent so the reagent is uniformly dispersed in the sampled feed stream. With the added reagent in the feed stream, the chemistry at the filter media in each of the filter portions 58, 58', 58", 58"' more accurately simulates the chemical changes that occur on the surface of the RO membrane. The adjustment in the zeta potential at the filter unit 20 also allows the apparatus to detect a wider range of foulants actually present on the surface of the RO membrane.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for monitoring the silt density index of a liquid feed stream flowing to a reverse-osmosis membrane comprising:

a filter unit through which at least a sample of the feed stream flows, said filter unit comprising a plurality of filter portions disposed hydraulically in parallel, and further comprising solenoid valves, in signal communication with said microprocessor-based controller, for selectively directing the sample feed stream to selected ones of said filter portions, whereby the sample feed stream is serially directed to successive ones of said filter portions;

a feed conduit for conveying to said filter unit the sample of the feed stream to be monitored;

a pressure regulator in said feed conduit for regulating a minimum pressure of the sample feed stream upstream of said filter unit;

a flow controller and a flow sensor for regulating a constant discharge of said sample feed stream in said conduit to said filter unit;

at least one pressure sensor for measuring the pressure of the sample feed stream on a side of said filter unit; and a microprocessor-based controller adapted to receive and process signals from said at least one pressure sensor to determine a rate of change in the pressure of the sample feed stream; wherein said pressure sensor signals said microprocessor-based controller when a selected maximum pressure is sensed, and said microprocessor-based controller initiates the closure of a first one of said solenoid valves and initiates the opening of a second one of said solenoid valves, in response to the signal from said at least one pressure sensor; and wherein further the rate of change in the pressure of the feed stream across successive ones of said filter portions provides data respecting the fouling rate of the reverse-osmosis membrane.

2. The apparatus of claim 1 further comprising means for modifying the zeta potential of the sample feed stream flowing into said filter unit, comprising:

a source of a chemical reagent in fluid communication with said feed conduit; and a pump for adding the chemical reagent from said source into said feed conduit, thereby to affect the chemistry of the sample feed stream.

3. The apparatus of claim 2 further comprising a mixer to uniformly disperse said chemical reagent in the sample feed stream.

4. The apparatus of claim 1 further comprising a temperature sensor in said feed conduit to measure temperature of the sample feed stream.

5. The apparatus of claim 1 further comprising means to vent trapped gasses from said filter unit.

6. The apparatus of claim 1 wherein said microprocessor-based controller monitors the flow rate of the sample feed stream, and monitors the pressure drop across said filter unit of said feed stream.

7. The apparatus of claim 6 wherein said microprocessor-based controller measures the pressure drop across said filter unit at prescribed times to perform SDI calculations.

8. The apparatus of claim 6 wherein said microprocessor-based controller measures the pressure drop across said filter unit at for selected periods of duration to perform SDI calculations.

9. The apparatus of claim 6 wherein said microprocessor-based controller is manually operable.

10. The apparatus of claim 6 wherein said microprocessor-based controller measures and stores SDI data.

11. The apparatus of claim 6 wherein said microprocessor-based controller further comprises at least one member selected from the group consisting of alarms, LCD data displays, relay outputs, and analog outputs.

12. The apparatus of claim 1 further comprising a means for separating and removing entrained gases within said feed stream.

13. The apparatus of claim 12, wherein said means for separating and removing entrained gases comprises a gas separation chamber and a vent disposed in said feed conduit.

* * * * *